(12) United States Patent
Shitara et al.

(10) Patent No.: US 8,294,888 B2
(45) Date of Patent: Oct. 23, 2012

(54) SURFACE DEFECT INSPECTION METHOD AND APPARATUS

(75) Inventors: Kenichi Shitara, Kamisato (JP); Hiroshi Nakajima, Hiratsuka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 39 days.

(21) Appl. No.: 12/855,873

(22) Filed: Aug. 13, 2010

(65) Prior Publication Data

US 2011/0075148 A1    Mar. 31, 2011

(30) Foreign Application Priority Data

Sep. 30, 2009   (JP) .................. 2009-227184

(51) Int. Cl.
    *G01N 21/00*  (2006.01)
(52) U.S. Cl. .................. 356/237.1; 356/237.2
(58) Field of Classification Search ..... 356/237.1–237.6
    See application file for complete search history.

(56) References Cited

U.S. PATENT DOCUMENTS

2008/0304057 A1 * 12/2008 Bills et al. .................. 356/237.5

FOREIGN PATENT DOCUMENTS

| JP | 3-186739 A | 8/1991 |
| JP | 5-21561 A | 1/1993 |

\* cited by examiner

*Primary Examiner* — Tri T Ton
(74) *Attorney, Agent, or Firm* — Mattingly & Malur, PC

(57) ABSTRACT

The present invention provides an apparatus and method which enable detecting a microscopic defect sensitively by efficiently collecting and detecting scattering light from a defect in a wider region without enlarging the apparatus. In the apparatus for inspecting a defect on a surface of a sample, including illumination means which irradiates a surface of a sample with laser, reflected light detection means which detects reflected light from the sample, and signal processing means which processes a detected signal and detecting a defect on the sample, the reflected light detection means is configured to include a scattering light detection unit which collects scattering light components of the reflected light from the sample by excluding specularly reflected light components by using an aspheric flannel lens and detecting the scattering light components.

7 Claims, 4 Drawing Sheets

SURFACE DEFECT INSPECTION METHOD AND APPARATUS

BACKGROUND

The present invention relates to a method and apparatus for inspecting for defects on the surface of a substrate for a magnetic disk and a semiconductor wafer. In particular, the invention relates to a surface defect inspection method and apparatus suitable for optically inspecting the surface of a substrate to detect dents and scratches on the surface and foreign matters attached to the surface.

An apparatus for optically inspecting for microscopic defects on the surface of a substrate for a magnetic disk and a semiconductor wafer is required to carry out higher speed and more sensitive inspection. To achieve more sensitive inspection, a method is adopted which includes increasing the intensity of illumination light by using laser as a light source and detecting light reflected from the substrate and scattering with a high sensitivity sensor, as described in, for example, Japanese Published Patent Application No. Hei 3-186739 and Japanese Published Patent Application No. Hei 5-21561. However, when the power or intensity of the illumination light is too strong, it will damage the substrate surface. Hence, reflected and scattering light from a defect on the substrate surface illuminated by the illumination light with limited irradiation intensity has to be detected with maximum detection sensitivity. As a configuration for detecting this reflected and scattering light with maximum detection sensitivity, the configuration adopting a photomultiplier unit is disclosed in Japanese Published Patent Application No. Hei 5-21561.

Scattering light from a microscopic defect has a characteristic in which, as the size of the defect becomes smaller, the amount of the scattering light from the defect per unit area decreases and this scattering light is more likely to diffuse across the whole space above the defect. Therefore, it is necessary to efficiently collect and detect the scattering light from the defect in a wider region in order to detect a microscopic defect sensitively using the illumination light with the same amount of light. To collect the scattering light in a wider region (solid angle), this can be accomplished by using a larger objective lens having a larger numeral aperture (NA) for collecting the scattering light from the substrate. However, employing a larger objective lens having a larger numeral aperture is limited in practice, in order that the objective lens should be prevented from interfering with other parts when installed in the inspection apparatus.

If a larger objective lens having a larger numeral aperture is employed, a converging lens through which the scattering light collected by the objective lens converges on the detector plane of a detector has to be larger accordingly. A set of these larger lenses requires larger lens barrels for supporting them, thus enlarging a detection optics system and making it difficult to make the apparatus smaller and lighter.

SUMMARY

An object of the present invention is to provide a surface defect inspection method and apparatus which solve the above problem of the prior art and enable identifying a microscopic defect sensitively by efficiently collecting and detecting scattering light from a defect in a wider region without enlarging the apparatus.

In order to achieve the above object, by using a structure combing aspheric flannel lenses or flannel lenses in a detecting optics system of a surface defect inspection apparatus, the present invention enables collecting and detecting scattering light from a defect in a wider region, processing a detected signal, and identifying a microscopic defect sensitively without enlarging the apparatus. It should be noted that, in the following description, the invention will be described taking some examples where aspheric lenses are used for reasons of expediency, but the use of spherical flannel lenses can also provide a similar effect.

Specifically, in an aspect of the present invention, apparatus for inspecting a defect on a surface of a sample is provided, including rotatable and movable table means on which a sample is mounted, an illumination means which irradiates a surface of the sample mounted on the table means with laser, reflected light detection means which detects reflected light from the sample irradiated with laser by the illumination means, and signal processing means which processes a signal output from the reflected light detection means by the detection of the reflected light and detects a defect on the sample, wherein the reflected light detection means is configured to include a scattering light detection unit which collects scattering light components of the reflected light from the sample by excluding specularly reflected light components by using an aspheric flannel lens and detects the scattering light components.

In another aspect of the present invention, an apparatus for inspecting a defect on a surface of a sample is provided, including a rotatable and movable table means on which a sample is mounted, first illumination and detection means which irradiates a surface of the sample mounted on the table means with first laser and detecting reflected light from the sample, second illumination and detection means which irradiates the surface of the sample mounted on the table means with second laser and detecting reflected light from the sample, and signal processing means which processes a signal output from the reflected light detection means by the detection of the reflected light and detecting a defect on the sample, wherein the first illumination and detection means is configured to include an illumination unit which irradiates the sample with laser and a scattering light detection unit which collects scattering light components of the reflected light from the sample irradiated with the laser by excluding specularly reflected light components by using an aspheric flannel lens and detects the scattering light components.

In another aspect of the present invention, an apparatus for inspecting a defect on a surface of a sample is provided, including rotatable and movable table means on which a sample is mounted, illumination means which irradiates a surface of the sample mounted on the table means with laser, reflected light detection means which detects reflected light from the sample irradiated with laser by the illumination means, and signal processing means which processes a signal output from the reflected light detection means by the detection of the reflected light and detects a defect on the sample, wherein the reflected light detection means is configured to include a scattering light detection unit which collects and detects scattering light components of the reflected light from the sample with the exclusion of specularly reflected light components by using plural aspheric flannel lenses disposed so as to surround virtually the whole surface above the table means.

In a further aspect of the present invention, a method for inspecting a defect on a surface of a sample is provided, including mounting a sample on a rotatable and movable table, irradiating a surface of the sample with laser while rotating and moving the table, detecting reflected light from the sample irradiated with the laser, and processing a signal obtained by detecting the reflected light and detecting a defect on the sample, wherein the method is adapted such that detecting the reflected light includes collecting scattering light components of the reflected light from the sample by excluding specularly reflected light components by using an aspheric flannel lens and detecting the scattering light components collected by using the aspheric flannel lens by a photoelectric converter.

In a further aspect of the present invention, a method for inspecting a defect on a surface of a sample is provided, including mounting a sample on a rotatable and movable table, irradiating a surface of the sample with first laser while rotating and moving the table, detecting first reflected light from the sample by the illumination of the first laser, irradiating the surface of the sample with second laser while rotating and moving the table, detecting second reflected light from the sample by the illumination of the first laser, and processing a signal obtained by detecting the first reflected light and a signal obtained by detecting the second reflected light and detecting a defect on the sample, wherein the step of detecting the first reflected light includes collecting first scattering light components of the first reflected light from the sample by excluding specularly reflected light components by using an aspheric flannel lens and detecting the first scattering light components collected by using the aspheric flannel lens by a photoelectric converter.

In a further aspect of the present invention, a method for inspecting a defect on a surface of a sample is provided, including mounting a sample on a rotatable and movable table, irradiating a surface of the sample with laser while rotating and moving the table, detecting reflected light from the sample irradiated with the laser, and processing a signal obtained by detecting the reflected light and detecting a defect on the sample, wherein the method is adapted such that detecting the reflected light includes collecting scattering light components of the reflected light from the sample by excluding specularly reflected light components by using plural aspheric flannel lenses disposed so as to surround virtually the whole space above the table and detecting the scattering light components collected by using the plural aspheric flannel lens by a photoelectric converter.

According to the present invention, it becomes possible to efficiently collect and detect scattering light from a defect in a wider region; therefore, the invention enables detecting more microscopic defects sensitively as compared with the prior art.

According to the present invention, by efficiently collecting and detecting scattering light from a defect in a wider region, sensitive detection of more microscopic defects can be accomplished without enlarging the apparatus.

These features and advantages of the invention will be apparent from the following more particular description of preferred embodiments of the invention, as illustrated in the accompanying drawings.

DESCRIPTION OF THE PREFERRED EMBODIMENTS

Examples of embodiments of the invention applied to a defect inspection apparatus for magnetic disks will be described below using the drawings.

[Embodiment 1]

Figure 1:
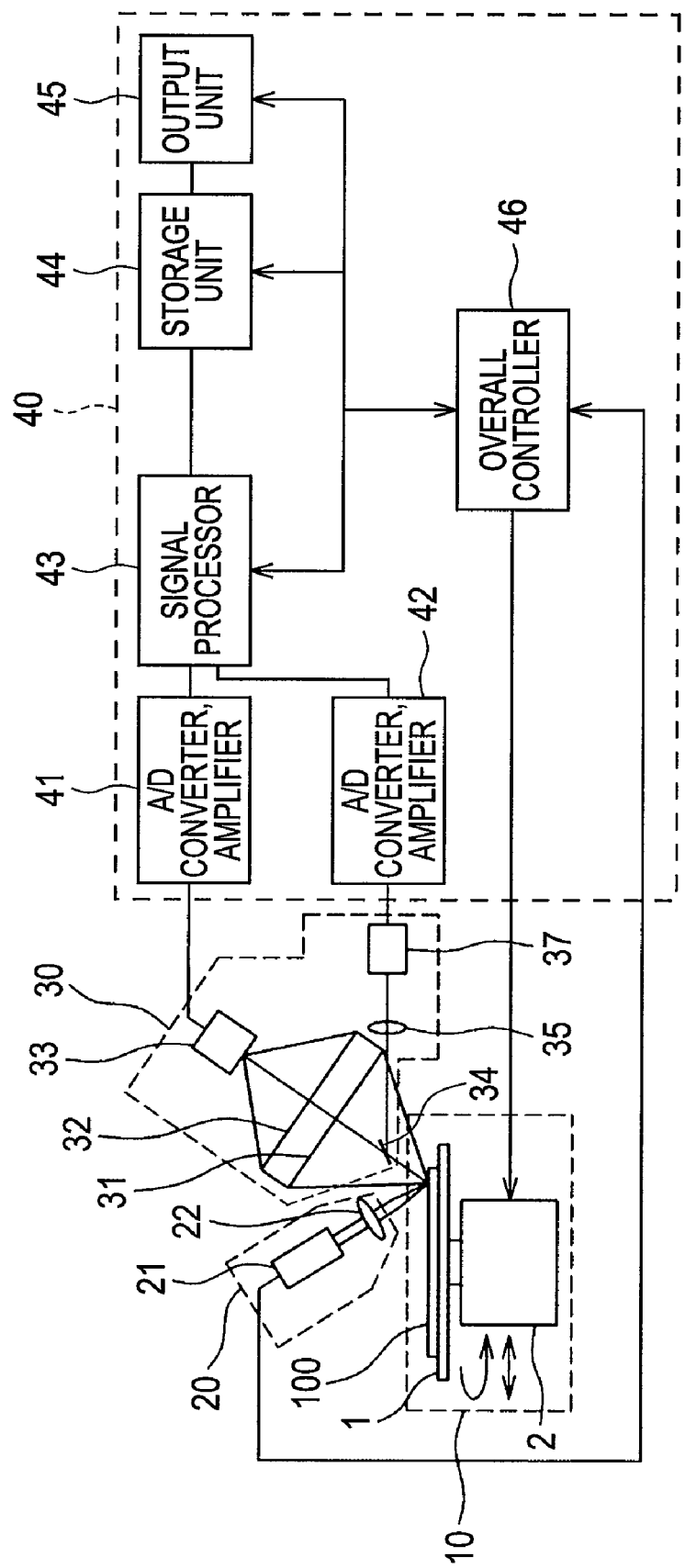
FIG. 1 is a block diagram showing a schematic structure of a surface defect inspection apparatus according to a first embodiment.

FIG. 1 is a diagram showing an overall structure of a defect inspection apparatus for magnetic disks according to Embodiment 1. The defect inspection apparatus is generally composed of a table section 10, an illumination optics system 20, a detection optics system 30, and a signal processing and control system 40.

The table section 10 includes a rotatable table 1 on which a sample 100 is mounted and a stage 2 capable to moving the table 1 in a direction perpendicular to a principal axis of rotation.

The illumination optics system 20 includes a laser source 21 and a converging lens 22 which converges laser emitted from the laser source 21 on the surface of the sample 100.

The detection optics system 30 includes a first aspheric flannel lens 31 corresponding to an objective lens which collects scattering light components of reflected light (specularly reflected light and scattering light) from the sample 100 illuminated by the illumination optics system 20, a second aspheric flannel lens 32 corresponding to a converging lens which converges the collected scattering light, a first photoelectric converter 33 (e.g., an avalanche photodiode (APD), a photomultiplier tube (PMT), or the like) which detects the scattering light converged by the second aspheric flannel lens 32 with high sensitivity, a mirror 34 which reflects specularly reflected light components of reflected light (which includes specularly reflected light and scattering light) from the sample 100 and changes the light path of the specularly reflected light, a collecting lens 35 which collects the specularly reflected light whose light path was changed by the mirror 34, and a second photoelectric converter 37 with plural detector elements (e.g., a photodiode array with plural pixels or an avalanche photodiode array) for detecting the collected specularly reflected light.

Figure 2A:
FIG. 2A is a cross-sectional view of an aspheric lens.
Figure 2B:
FIG. 2B is a cross-sectional view of an aspheric flannel lens having the same aperture as for the lens shown in FIG. 2A.

FIG. 2A shows a commonly used aspheric optical lens 310 and FIG. 2B shows an example of an aspheric flannel lens 320 having the same aperture as the lens 310. As can be seen from these figures, the thickness of the aspheric flannel lens 320 can be made relatively thinner than the commonly used aspheric optical lens 310 having the same aperture. In the present embodiment, aspheric flannel lenses having this feature are used as the first aspheric flannel lens 31 and the second aspheric flannel lens 32.

The signal processing and control system 40 includes a first A/D converter 41 which analog-to-digital converts and amplifies an output of the first photoelectric converter 33, a second A/D converter 42 which analog-to-digital converts and amplifies an output of the second photoelectric converter 37, a signal processor 43 which receives outputs of the first A/D converter 41 and the second A/D converter 42 and performs signal processing on them, a storage unit 44 which stores results of processing performed by the signal processor 43, an output unit 45 with a display screen on which results of processing performed by the signal processor 43 are output, and an overall controller 46 which controls the whole of the apparatus.

Then, the operation of each section/system is described. Controlled by the overall controller 46, the table section 10 rotates the table 1 with a sample 100 mounted thereon and moves the stage 2 in a direction perpendicular to the principal axis of rotation in synchronous with the rotation of the table 1.

While the sample 100 is rotated and moved by the table section 10, laser emitted from the laser source 21 in the illumination optics system 20 being controlled by the overall controller 46 is converged on the surface of the sample 100 by the converging lens 22 to irradiate the surface of the sample 100.

From the surface of the sample 100 irradiated with laser, reflected light (including scattering light and specularly reflected light) arises, influenced by the surface condition, e.g., a defect or a scratch present on the surface and minute concavity and convexity (unevenness) of the plane. At this time, the scattering light is subjected to dispersion depending on the size of the defect on the surface. That is, the scattering light from a large defect or scratch is subjected to directional dispersion with relatively large intensity, whereas the scattering light from a small defect or scratch is subjected to isotropic dispersion with relatively small intensity.

Specularly reflected light components of the reflected light from the surface of the sample 100 irradiated with laser are reflected by the mirror 34 disposed (on the path of the specularly reflected light) at the same outgoing angle with respect to the sample as the angle of incidence of the incoming laser to the sample 100. The specularly reflected light components are then directed to the collecting lens 35 and collected through the collecting lens 35 to enter an imaging lens 36 which forms the image of the specularly reflected light on the imaging plane of the second photoelectric converter 37. In this way, the specularly reflected light components are detected (imaged) by the second photoelectric converter 37. The mirror 34 is formed to have a sufficiently small shape so as not to reflect light components (scattering light components) other than the specularly reflected light components.

On the other hand, of the reflected light from the surface of the sample 100 irradiated with laser, the light components (scattering light components) not reflected by the mirror 34, which entered the first aspheric flannel lens 31 serving as the objective lens, are collected to enter the second aspheric flannel lens 32 serving as the converging lens. The scattering light components are then converged on the detector plane (not shown) of the first photoelectric converter 33 and detected by the first photoelectric converter 33 with high sensitivity.

Here, it should be noted that the first aspheric flannel lens 31 and the second aspheric flannel lens 32 are thinner and lighter than conventional optical lenses. Thus, the lens barrels (not shown) within which these lenses are mounted can be made relatively compact, as compared with those for the conventional optical lenses. This increases the flexibility of design in terms of where these lenses should be disposed above the sample and makes it possible to design the detection optics system with a numeral aperture (NA) of 0.6 or more (the NA is limited to 0.4 or less for the system when using the conventional optical lenses).

Since the scattering light from a small defect distributes isotropic dispersion above the substrate and the level of a detected signal is proportional to the area of the detector plane, the detection optics system of the present embodiment is able to obtain signal larger than the signal obtained by the same system using the conventional optical lenses when the detection sensitivity is comparable. In other words, the detection optics system of the present embodiment is able to detect scattering light from a smaller defect than the conventional system, when compared at the same level of detected signal.

Each of the A/D converters 41 and 42 converts an analog signal output from the first photoelectric converter 33 or the second photoelectric converter 37 into a digital signal and amplifies and outputs the digital signal.

The digital signals output from the A/D converters 41 and 42 are input to the signal processor 43. The signal processor 43 performs processing on the digital signals corresponding to both or either of the output signal from the first photoelectric converter 33 and the output signal from the second photoelectric converter 37. Thereby, the signal processor 43 detects a defect existing on the surface of the sample 100 and locates the detected defect on the substrate 100, using information for a laser irradiation position on the sample 100 obtained from the overall controller 47 which controls the table section 10. Further, the signal processor 43 identifies the type of the detected defect, based on the characteristics of the detected signals from the first photoelectric converter 33 and the second photoelectric converter 37.

Figure 3A:
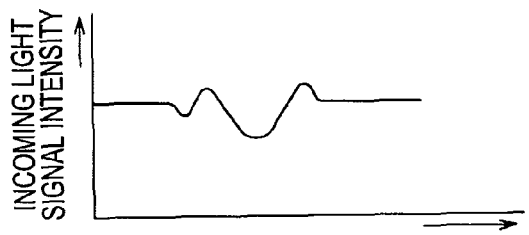
FIG. 3A is a graph showing an example of an output signal of a second photoelectric converter 37 in the first embodiment, representing dispersion in the intensity of reflected light from a region including a moderate convex defect.
Figure 3B:
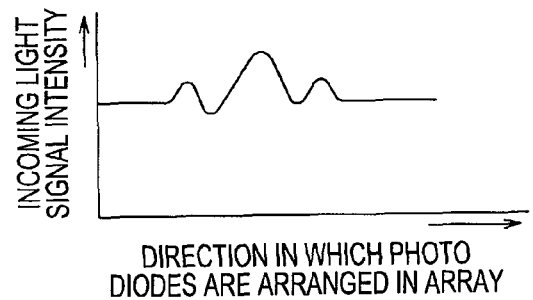
FIG. 3B is a graph showing an example of an output signal of the second photoelectric converter 37 in the first embodiment, representing dispersion in the intensity of reflected light from a region including a moderate concave defect.
Figure 4:
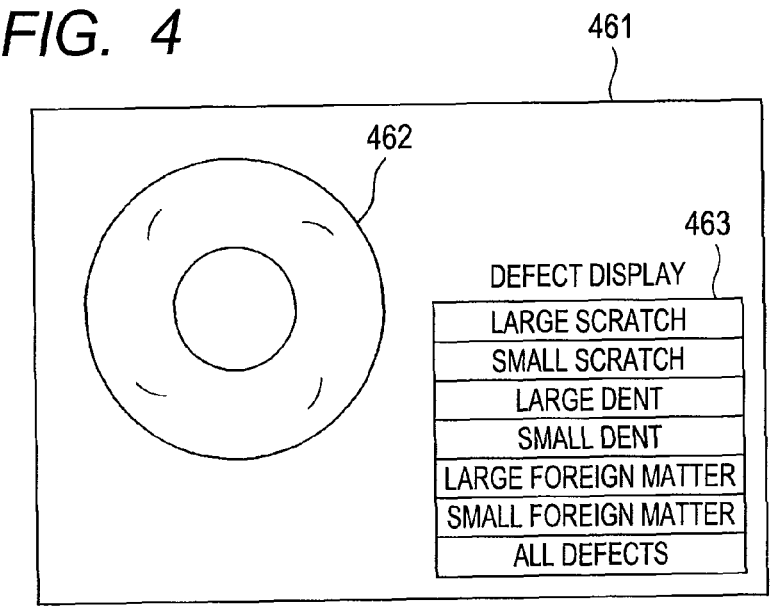
FIG. 4 is a front view of a display screen showing a GUI output example of an inspection result in the first embodiment.

The detection optics system provided with the second photoelectric converter 37 detects the specularly reflected light components from the sample 100 collected by the collecting lens 35. The second photoelectric converter 37 may include plural detector pixels arranged in an array to detect a change and a deviation (dispersion) in the intensity of reflected light from the sample 100 having a defect, if any, collected by the collecting lens 35. FIG. 3A represents dispersion in the intensity of reflected light from a region including a moderate convex defect and FIG. 3B represents dispersion in the intensity of reflected light from a region including a moderate concave defect. From these graphs, it is apparent that the intensity of the reflected light from a region including a moderate convex defect decreases, whereas the intensity of the reflected light from a region including a moderate concave defect increases.

Meanwhile, although not shown in FIGS. 3A and 3B, dispersion in the intensity of specularly reflected light from a region where a foreign matter is attached to the surface of the sample 100 decreases like the dispersion in the reflected light from a region including a moderate convex defect. However, the dispersion in this case is broader (i.e., more elements in the array are used to detect the dispersion in the reflected light intensity) than the dispersion of specularly reflected light from a region including a moderate convex defect.

In this way, the dispersion of specularly reflected light from the sample 100 occurs in different manners depending on the type of a defect. By analyzing the characteristics of such dispersion of reflected light intensity, it is thus possible to identify a concave defect, a convex defect, or a foreign matter.

Using numerical information of number of pixels of the first photoelectric converter 33 and the second photoelectric converter 37 which detect the reflected light from the sample 100, it is also possible to determine a rough size category (e.g., large, medium, small) of each defect detected.

Results determined by the signal processor 43 are stored into the storage unit 44 in association with position information for a defect. In addition, these results are displayed in a map form 462 on the screen 461 of the output unit 46 such that a defect(s) selected by a defect display selector 463 can be identified according to type and size.

According to the present embodiment, scattering light from microscopically smaller defects can be detected, as compared with the conventional system. Taking an example of detecting a scratch defect, while the detection optics system using conventional optical lenses is only able to detect a defect with a size on the order of several hundred nanometers (nm), the detection optics system according to the present embodiment is able to detect a defect with a size on the order of one hundred nanometers (nm).

Further, according to the present embodiment, a compact detection optics system with a higher NA can be configured using the combination of aspheric flannel lenses and it is thus possible to detect microscopic defects without enlarging the apparatus.

[Embodiment 2]

As a second embodiment, an inspection apparatus equipped with plural detection optics systems as a combination of the optics system described in the first embodiment and a conventional optics system is described using the related drawings.

Figure 5A:
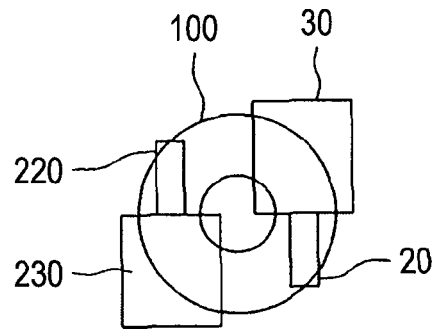
FIG. 5A is a planar block diagram showing a schematic structure of an inspection apparatus according to a second embodiment.
Figure 5B:
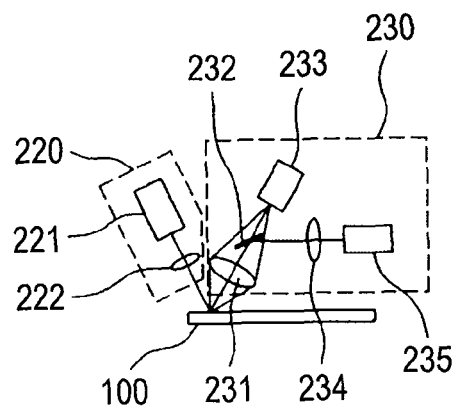
FIG. 5B is a front block diagram showing a schematic structure of an illumination optics system 220 and a detection optics system 230 of the inspection apparatus according to the second embodiment.

FIG. 5A shows a plan view of a structure in which the illumination optics system 20 and the detection optics system 30 according to the present invention is combined with a conventional illumination optics system 220 and a detection optics system 230. Meanwhile, FIG. 5B shows a front view of the conventional illumination optics system 220 and the detection optics system 230.

The structure of the illumination optics system 20 according to the present invention and the structure of the conventional illumination optics system 220 including a laser source 221 and a collecting lens 222 are basically the same.

Outputs from both the detection optics system 230 and the detection optics system 30 are processed by a signal processor having a structure corresponding to the signal processing and control system 40 described in the first embodiment and a defect is detected. However, the structure corresponding to the signal processing and control system 40 is omitted from FIG. 5B for simplicity and to avoid repeated description.

The detection optics system 230 of the prior art is configured such that components of light reflected from a sample 100 and passing through an objective lens 231, i.e., reflected light (scattering light) components whose light path is not changed by a mirror 232 are detected by an photoelectric conversion element 233. Meanwhile, specularly reflected light components from the sample 100 whose light path is changed by the mirror 232 are collected by a lens 234 to converge on the detector plane of a light receiving element 235 and detected.

A relation between a laser irradiation position on the sample 100 by the illumination optics system 220 and a laser irradiation position on the sample 100 by the illumination optics system 20 is adjusted in advance. The sample 100 is illuminated by the illumination optics system 220 and the illumination optics system 20 at the same time and respective reflected lights from the sample are detected by the detection optics system 230 and the detection optics system 30. Respective signals thus detected are confronted with each other so that detected signals from the same defect can be identified and processed, as their positional relation on the sample 100 is determined in the pre-adjustment step.

Figure 6:
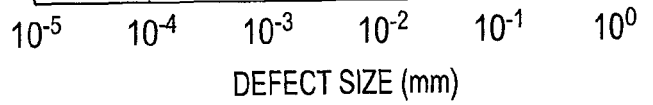
FIG. 6 is a graph showing a range 601 in which defects are detected by the detection optics system 230, a range 602 in which defects are detected by a detection optics system 30, and a range 603 in which defects are detected by the combination of the detection optics systems 230 and 30 in the second embodiment.

As a result, it is possible to combine a detectable range 601 (from several hundred nanometers (nm) to several hundred micrometers (μm)) by the detection optics system 230 with a detectable range 602 (from several tens of nanometers (nm) to several hundred micrometers (μm)) by the detection optics system 30, as is shown in FIG. 6. A range 603 in which defects can be detected by the apparatus as a whole can be extended as compared with a case where the detection optics system 230 or the detection optics system 30 is used singly.

[Embodiment 3]

As a third embodiment, an example in which the apparatus is configured such that virtually the whole space above a sample 100 is surrounded by aspheric flannel lenses described in the first embodiment is described using the related drawings.

Aspheric flannel lenses can be made of plastics and can be manufactured into an arbitrary form using plastic material. These lenses are light because they are made of plastic material. When plural aspheric flannel lenses are coupled and used, joint members for coupling them only need to have less strength than those that are used to couple ordinary glass lenses. Therefore, an assembly of aspheric flannel lenses can be manufactured into a relatively thin structure.

To increase the sensitivity in detecting defects, as much scattering light from a defect as possible should be collected and detected by a high sensitivity photoelectric converter.

As already stated, scattering light from a defect has characteristics in which, as the size defect becomes smaller, the scattering light from the defect is more likely to spread all directions above the defect. Hence, it is good for using an integrating sphere to collect this scattering light efficiently. However, the integrating sphere collects stray light near the surface together with the scattering light, which results in a decrease in the S/N ratio of detected signals. For commonly used integrating spheres, the reflectance of their inner wall does not reach 100% completely and the sizes of an incident light window, an outgoing light window, and a sample window result in a decrease in the light collection efficiency. Consequently, the total light collection efficiency (the proportion of incident light at the detector in the light reflected from a sample 100) decreases to 50% or lower.

Figure 7A:
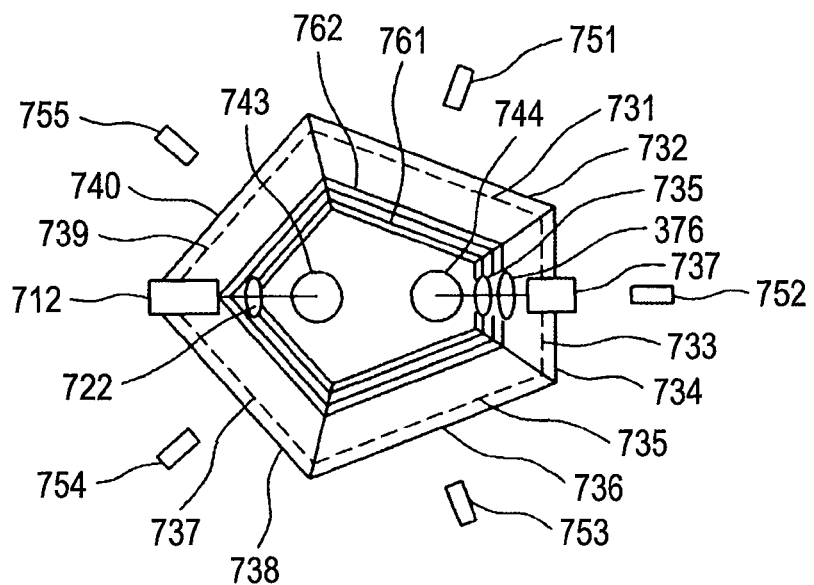
FIG. 7A is a plan view showing a schematic structure of an inspection apparatus in a third embodiment.

Therefore, in the present embodiment, an assembly of plural aspheric flannel lenses 731 to 742 having a polyhedral structure, as is shown in FIG. 7A (a hexahedron as in FIG. 7A), is used as an optics system that has light collection efficiency equivalent to or higher than that of an integrating sphere. And the optics system has a capability of detecting a defect from which directional scattering light is reflected and collecting light scattered from a defect while excluding stray light. More specifically, an inner polyhedron which corresponds to an objective lens is made up of aspheric flannel lenses 731, 733, 735, 737, 739, and 741 and an outer polyhedron which corresponds to a converging lens is made up of aspheric flannel lenses 732, 734, 736, 738, 740, and 742. The aspheric flannel lenses 731, 733, 735, 737, 739, and 741 constituting the inner polyhedron are coupled with join members 761 and the aspheric flannel lenses 732, 734, 736, 738, 740, and 742 constituting the outer polyhedron are coupled with join members 762.

Because of the relatively thin structures of the joint members 761 and 762, there can be a smaller area that shades scattering light from a sample 100 to be detected and light collection efficiency of 80% can be ensured. (For example, it is possible to form the inner and outer polyhedral structures by cutting and forming a plastic sheet into the aspheric flannel lenses 731 to 741 and boding these plastic sheet lenses together using a transparent adhesive agent.)

In this polyhedral assembly, laser emitted from a laser source 721, after passing through a collecting lens 722, passes through holes 743 provided in top-plane aspheric flannel lenses 741 and 742 and irradiates the surface of a sample 100 in the central position of the polyhedral assembly. Specularly reflected light components of reflected light from the surface of the sample 100 pass through holes 744 provided in the top-plane aspheric flannel lenses 741 and 742 and enter an objective lens 735. Then, through an imaging lens 736, the image of the specularly reflected light is formed on the imaging plane of a photoelectric converter 737 and thus detected.

On the other hand, scattering light components of the reflected light from the sample 100, diffusing across the whole space above the sample, enter the inner aspheric flannel lenses 731, 733, 735, 737, 739, and 741 of the polyhedral assembly, disposed to surround virtually the whole space above the sample 100, and are then converged through the aspheric flannel lenses 732, 734, 736, 738, 740, and 742 constituting the outer polyhedral structure which corresponds to the converging lens.

To the conjugate points of the respective aspheric flannel lenses 732, 734, 736, 738, 740, and 742, one ends of glass fibers 751 to 756 are connected, respectively, through which incoming scattering light components go out from the other ends of the glass fibers 751 to 756 and detected by a photoelectric converter 757 with high sensitivity installed in front of the other ends of the gals fibers. By thus connecting the one ends of the glass fibers 751 to 756 to the conjugate points of the respective aspheric flannel lenses 732, 734, 736, 738, 740, and 742, it is possible to prevent stray light from entering the one ends of the glass fibers 751 to 756 and prevent the S/N ratio of detected signals from decreasing.

As a result of detecting scattering light by this photoelectric converter 757, obtained signals are processed in the same way as in the first embodiment and, therefore, description thereof is omitted.

Figure 7B:
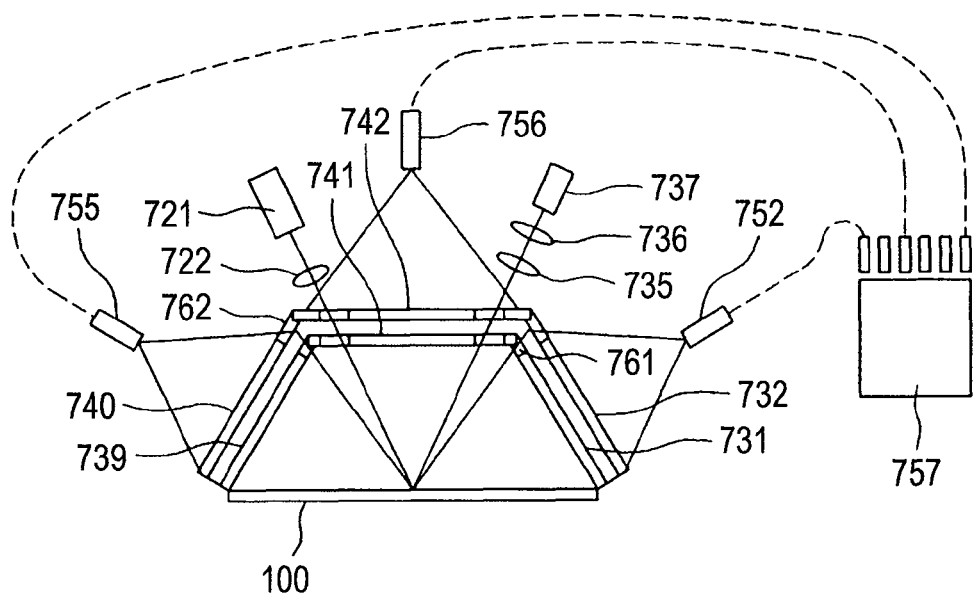
FIG. 7B is a front view showing the schematic structure of the inspection apparatus in the third embodiment.

In the structure shown in FIGS. 7A and 7B, a subassembly of the inner aspheric flannel lenses 731, 733, 735, 737, 739, and 741 of the polyhedral assembly and a subassembly of the aspheric flannel lenses 732, 734, 736, 738, 740, and 742 constituting the outer polyhedral structure are disposed so as to be spaced apart from each other. Alternatively, the subassembly of the inner aspheric flannel lenses of the polyhedral assembly and the subassembly of the aspheric flannel lenses constituting the outer polyhedral structure may be disposed so as to contact each other.

In the present embodiment, the apparatus is configured such that the one ends of the glass fibers 751 to 756 are placed on the conjugate points of the respective aspheric flannel lenses 732, 734, 736, 738, 740, and 742 and scattering light components entering the glass fibers 751 to 756 are directed to the photoelectric converter 757 with high sensitivity. Alternatively, the apparatus may be configured such that, instead of the glass fibers 751 to 756, light shielding plates provided with pin holes to shade stray light may be installed at the conjugate points of the respective aspheric flannel lenses 732, 734, 736, 738, 740, and 742 and light components passing through the pin holes of the light shielding plates are detected by photoelectric converters with high sensitivity which are installed behind each of the shielding plates. In this case, six photoelectric converters are needed, but by processing their outputs separately, it becomes possible to obtain information on scattering directionality for each defect. It is possible to use such information which is useful to improve the accuracy of classifying detected defects.

According to the present embodiment, by detecting scattering light from a sample 100 with relatively high light collection efficiency, it is possible to obtain signals with a high S/N ratio, thereby enabling to detect microscopically smaller defects (several tens of nanometers or more).

Although the examples in which aspheric flannel lenses are used have been described in the foregoing Embodiments 1 through 3, these lenses may be replaced by spherical flannel lenses.

The invention may be embodied in other specific forms without departing from the spirit or essential characteristics thereof. The present embodiments are therefore to be considered in all respects all illustrative and not restrictive, the scope of the invention being indicated by the appended claims, rather than by the foregoing description, and all changes which come within the meaning and range of equivalency of the claims are therefore intended to be embraced therein.

The invention claiimed is:

1. An apparatus for inspecting a defect on a surface of a sample, comprising:
   rotatable and movable table means on which a sample is mounted;
   illumination means which irradiates a surface of the sample mounted on the table means with a laser;
   reflected light detection means which detects reflected light from the sample irradiated with the laser by the illumination means; and
   signal processing means which processes a signal output from the reflected light detection means by the detection of the reflected light and detecting a defect on the sample,
   wherein the reflected light detection means includes a scattering light detection unit which collects scattering light components of the reflected light from the sample by excluding specularly reflected light components by using an aspheric flannel lens which has a greater numerical aperture than a conventional optical lens when installing the conventional optical lens instead of the aspheric flannel lens and detects the scattering light components from a smaller defect than the conventional optical lens when installing the conventional optical lens instead of the aspheric flannel lens.

2. The apparatus for inspecting a defect on a surface of a sample according to claim 1, wherein the scattering light detection unit of the reflected light detection means includes a first aspheric flannel lens to collect scattering light components from the sample, a second aspheric flannel lens to converge the scattering light components collected by the first aspheric flannel lens, and a photoelectric converter to detect the scattering light components converged by the second aspheric flannel lens.

3. The apparatus for inspecting a defect on a surface of a sample according to claim 2, wherein the first aspheric flannel lens and the second aspheric flannel lens are disposed so as to contact each other.

4. The apparatus for inspecting a defect on a surface of a sample according to claim 1, wherein the reflected light detection means further includes a specularly reflected light detection unit which extracts specularly reflected light components out of the reflected light from the sample and detects the extracted specularly reflected light components.

5. A method for inspecting a defect on a surface of a sample, comprising the steps of:
  mounting a sample on a rotatable and movable table;
  irradiating a surface of the sample with a laser while rotating and moving the table;
  detecting reflected light from the sample irradiated with the laser; and
  processing a signal obtained by detecting the reflected light and detecting a defect on the sample,
  wherein the step of detecting reflected light includes collecting scattering light components of the reflected light from the sample by excluding specularly reflected light components by using an aspheric flannel lens which has a greater numerical aperture than a conventional optical lens when installing the conventional optical lens instead of the aspheric flannel lens and detecting the scattering light components collected from a smaller defect than the conventional optical lens when installing the conventional optical lens instead of the aspheric flannel lens.

6. The method for inspecting a defect on a surface of a sample according to claim 5, wherein collecting the scattering light components by using the aspheric flannel lens includes collecting the scattering light components by a first aspheric flannel lens, converging the scattering light components collected by the first aspheric flannel lens by a second aspheric flannel lens, and detecting the scattering light components converged by the second aspheric flannel lens by the photoelectric converter.

7. The method for inspecting a defect on a surface of a sample according to claim 5, wherein the step of detecting reflected light further includes detecting specularly reflected light components excluded from the reflected light from the sample and the step of detecting a defect on the sample further includes processing a signal obtained by detecting the scattering light components and a signal obtained by detecting the specularly reflected light components and detecting a defect on the sample.

* * * * *